United States Patent [19]

Tetzlaff

[11] Patent Number: 5,001,352

[45] Date of Patent: Mar. 19, 1991

[54] METHOD AND APPARATUS FOR IRRADIATING OBJECTS WITH IONIZING RADIATION

[76] Inventor: Karl H. Tetzlaff, Mörikestr. 6, 6233 Kelkheim, Fed. Rep. of Germany

[21] Appl. No.: 508,544

[22] Filed: Apr. 16, 1990

Related U.S. Application Data

[63] Continuation of Ser. No. 361,743, May 30, 1989, abandoned, which is a continuation of Ser. No. 210,184, Jun. 22, 1988, abandoned, which is a continuation of Ser. No. 55,713, filed as PCT DE86/00388 on Sept. 23, 1986, published as WO87/01861 on Mar. 26, 1987, abandoned.

[30] Foreign Application Priority Data

Sep. 23, 1985 [DE] Fed. Rep. of Germany ....... 3533825

[51] Int. Cl.$^5$ ............................................. G01N 21/00
[52] U.S. Cl. .................................... 250/453.1; 378/69; 250/454.1
[58] Field of Search ............... 250/453.1, 454.1, 455.1; 378/69

[56] References Cited

U.S. PATENT DOCUMENTS

| | | | |
|---|---|---|---|
| 3,142,759 | 7/1964 | Jefferson et al. | 378/69 |
| 3,641,342 | 2/1972 | Armel et al. | 378/69 |
| 3,676,675 | 7/1972 | Ronsohoff | 250/454.1 |
| 4,029,967 | 6/1977 | Tetzloff | 378/69 |
| 4,066,907 | 1/1978 | Tetzloff | 378/69 |

FOREIGN PATENT DOCUMENTS 1286598 1/1962 France ............................... 378/69

Primary Examiner—Bruce C. Anderson
Attorney, Agent, or Firm—Cushman, Darby & Cushman

[57] ABSTRACT

A process and an apparatus for the irradiating objects by ionizing irradiation, in particular with an X-ray or gamma ray source of radiation, whereby the objects are packed in shipping units having a symmetry of axis running parallel to the direction of conveyance or parallel to the longest extension of the source of radiation. Some of the objects are brought to a position near another object and placed at a distance from the source of radiation, so that near objects partially shield the distant objects from the radiation source in such a manner that the shielding effect is less near the axis of symmetry than in the peripheral area. The objects are moved in such a way that they are irradiated from at least two sides. By this means greater efficiency and excellent uniformity of the absorbed radiation are achieved.

27 Claims, 8 Drawing Sheets

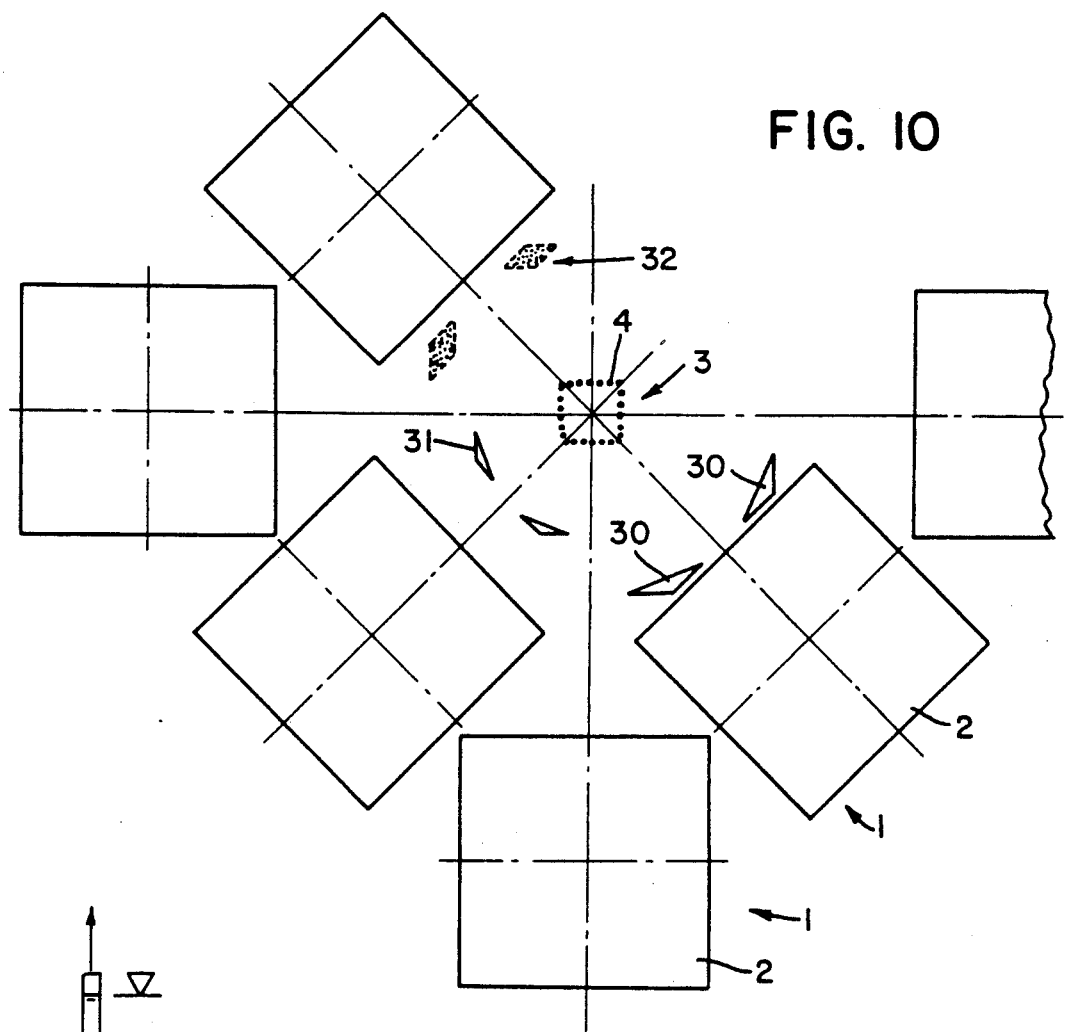
FIG. 10
FIG. 12
FIG. 11

METHOD AND APPARATUS FOR IRRADIATING OBJECTS WITH IONIZING RADIATION

This is a continuation of application Ser. No. 361,743, filed May 30, 1989, which was abandoned upon the filing hereof, which was a continuation of application Ser. No. 07/210,184, filed June 22, 1988, which was a continuation of application Ser. No. 07/055,713, filed as PCT DE86/00388 on Sept. 23, 1986, published as WO87/01861 on Mar. 26, 1987, now abandoned.

BACKGROUND OF THE INVENTION

The invention relates to a process and an apparatus for irradiating objects, which have been packaged in shipping containers with ionizing sources of radiation, such as X-rays or gamma rays.

Such processes are used for sterilizing disposable health care articles or treating foodstuffs.

BACKGROUND OF THE INVENTION

To be practical in industrial applications, irradiations should be done as uniformly as possible and with large packaging units with high irradiation efficiency. Radiation efficiency is the term given to the ratio of the utilized radiation to the total emitted radiation. The utilized radiation relates to the minimal dosage in a shipping unit. The emitted radiation which exceeds this minimal dosage thus must be regarded as wasted.

According to German Patent No. 2,358,652 and the ATOMKERNENERGIE/KERNTECHNIK 34 (1979) 4, 305/308 there is an apparatus in which large shipping units stacked in columns are arranged in a circle around a rod-shaped radiation source while the columns rotate about their axis of symmetry. Shielding elements partially shield the peripheral area of the objects and are placed laterally of the path of radiation from the radiation source and of the axis of rotation. This technique prevents a large part of the radiation in needlessly overdosing the peripheral area. Instead the shields absorb this comparatively large part of the radiation. The apparatus described in German Patent No. 2,358,652 simultaneously irradiates several products for varying lengths of time. This multiple purpose feature is of great importance in industrial practice.

SUMMARY OF THE INVENTION

An object of the present invention essentially is to increase their irradiation efficiency over prior art processes or prior art apparatuses without forfeiting the multiple purpose feature hereinbefore.

According to an aspect of the invention, this object is accomplished in that the objects to be irradiated are brought to a position near the source of radiation, whereby some of the objects near the source shield other objects positioned at a distance from the source in such a manner that the shielding effect is less in the area near the axis of symmetry than in the peripheral area. Further the objects are moved in such a manner that they are irradiated from at least two sides.

In this way, adjacent objects function as shields for a specific period of time, whereby the movement frequency is selected so that the objects function as shields at least once.

Accordingly, radiation otherwised absorbed by the shielding units is exploited since the objects to be irradiated temporarily function as shielding elements.

An apparatus to carry out this aspect of the invention comprises a source of radiation around which at least four shipping units of objects are arranged on at least four transport devices, and at least two shipping units are placed in a position near the source of radiation and at least two shipping units are placed at a distance from the source so that the objects near the radiation source shield the distant objects in such a manner that the shielding effect in the center of the objects is less than in the peripheral area.

Sources of radiation may be any source emitting ionizing radiation which can be used for the respective purpose and in particular radionuclides or X-ray radiation sources.

Especially good results are attained by irradiating the objects to be irradiated from four sides. Furthermore, the objects may be rotated continuously, pendulantly or in steps so that the objects are irradiated from more than four directions.

In small irradiation plants, the shipping units can be moved individually one after the other or in groups simultaneously. In large irradiation plants it is expedient to place several shipping units closely side by side or to stack them closely. Each shipping unit can be individually supported by a carrying device. Such an arrangement is referred to herein as a column. A vertical column can consist by way of illustration of a narrow rack having several tiers on which pallets with objects to be irradiated are stacked one on top of the other. The vertical axis of symmetry of the column is referred to as the axis of rotation of the column or the axis of rotation, even when the column consists of only one shipping unit. Very good results are achieved when the axes of rotation of the columns run parallel to a rod-shaped source of radiation and/or in the direction of conveyance in which the objects to be irradiated are transported past any radiation source as this process has the same effect as a rod-shaped source of radiation. A vertical orientation of the axis of rotation of the column is not imperative. The axis of rotation may be oriented in any direction.

The manner in which the irradiated objects are brought to the two positions near to and far from the radiation source does not influence irradiation efficiency or dosage uniformity significantly. There are two basic methods of conveyance. One is a particularly simple method in which the objects to be irradiated are placed on stationary, immobile carrying devices, by way of illustration rack tiers. The objects can then be rearranged in the manner of the invention, by way of illustration, with an automatic rack handling device. The objects must thus be placed in the near and distant positions, rotated and depending on the geometric shape of the radiation sources, must be conveyed in the direction of the axis of rotation of the column. Due to the great number of movements, this process is not particularly suitable for large throughputs. Another method is to move several columns with several shipping units in both end positions, whereby at least half of the columns can be moved simultaneously. In these positions or in easily reached auxiliary positions, the columns can also be rotated around their own axes of symmetry.

A simple method to reach both end positions is to move the columns to and fro, by way of illustration on rails, in a radial direction to the source of radiation (claim 3). This process is particularly easy to modify. For example, the end positions and the movements may be easily altered and individually regulated. On the whole, a rod-shaped source of radiation and/or in the direction of conveyance in which the objects to be irradiated are transported past any radiation source, as this process has the same effect as a rod-shaped source of radiation. A vertical orientation of the axis of rotation of the column is not imperative. The axis of rotation may be oriented in any direction.

For a complete irradiation process the objects to be irradiated must take up at least one position near the radiation source and one position at a distance from the radiation source and be irradiated from at least two sides. For a complete irradiation process several such movement cycles can also be carried out. It is useful to select a large cycle frequency when products are to be irradiated simultaneously with great varying dosages and/or the density of the products differs considerably. The length of the cycle, however, need not be constant. It is particularly advantageous if the cycle period is regulated in such a manner that one movement cycle is just completed between two removals of the objects to be irradiated from any column. In the case of a long source of radiation having suitable activity distribution, all the objects of a column can be loaded and unloaded each time. Greater efficiency, however, is achieved with a shorter radiation source when the objects traverse the column in the direction of the axis of rotation continuously or in steps. This rearranging can be carried out by means of a rack handling device. The axis of rotation of the column is preferably vertical. It can, however, also be horizontal. This facilitates transporting the objects to be irradiated continuously, by way of illustration with the aid of a roller bed conveyor.

Especially high efficiency is achieved when the objects are arranged in such a manner that there is an empty space near the axis of rotation of the column. Similar efficiency and excellent uniformity of dosage is attained when the objects are arranged so that the density of the objects is great in the outer area of the cross-section and less near the axis of rotation of the column. Less density in the center can be attained, by way of illustration, by means of the packaging of the same product, however, with larger gaps. These measures are especially effective in the case of very voluminous shipping units with great density.

Dosage uniformity which is quite good even without any special measures can be further improved in columns with rectangular cross-sections by special process measures and modifications of the apparatus. Utilization of this improvement is particularly advantageous when objects of greatly varying density are to be irradiated simultaneously. Special process measures that can result in improved dosage uniformity are as follows:
- a pendulant rotational movement of the column in order to prevent minimum dosage in the corners,
- the selection of a non-uniform rotational velocity in order to bring the corners closer to the source of radiation for a longer period of time,
- changing the end positions in order to set the right shielding effect
- the installation of several intermediate stops or a variable moving velocity on the path in order to dose the shielding effect.

By appropriate modification of the apparatus, dosage uniformity can be increased further particularly by means of additional shielding devices or by means of a special distribution of the activity over the cross-section of the radiation source. An especially advantageous activity distribution is attained with the formation of a symmetrical n-cornered structure, whereby "n" is the number of columns, an integral part thereof or an integral multiple thereof. Also advantageous is a continuous or step by step rotational movement of the radiation source. Dosage uniformity and efficiency can also be improved by arranging the individual elements of the radiation source in subgroups and moving these toward each other. This is particularly advantageous when the objects are placed very close to the source of radiation.

Furthermore, additional shielding devices may preferably be arranged so that they additionally weaken the radiation lateral of the line from the radiation source and the axis of rotation of the column. The shielding devices, which can be made of metal sheet, can be arranged in such a way that they rotate with the column or are fixed stationary between the radiation source and the column. They can be assigned to the near column and/or the distant column position. Moveable shielding devices are also advantageous in coordination with the pendulant rotational movement of the columns. When daily changing non-uniform sortiments of products are to be irradiated, it is especially advantageous to employ a multiplicity of thin-walled pipes standing closely together which, depending on the products to be irradiated, are filled with a fluid as a shielding device. In this way the site and form of the effective additional shielding can be changed rapidly.

A further embodiment of the present invention is that a program control can be provided to set the optimum radiation parameters which initiates all the movements. Particularly advantageous is flexible control by means of a process computer which contains an algorithm to calculate the doses in advance taking into consideration the adjacent columns and the shielding devices. Depending on the given priority, the plant can be regulated to attain the best dosage uniformity, the best efficiency or an optimum of both. The control can also be supported by measuring the dosage rates at suitable sites.

BRIEF DESCRIPTION OF THE DRAWINGS

The present invention is made more apparent in the following detailed description of preferred embodiments of the invention with reference to the drawings in which;

FIG. 10 shows an arrangement having various shielding devices;

FIGS. 11 and 12 show details of the shielding devices of FIG. 10; and

DESCRIPTION OF ILLUSTRATIVE EMBODIMENTS

Figure 1:
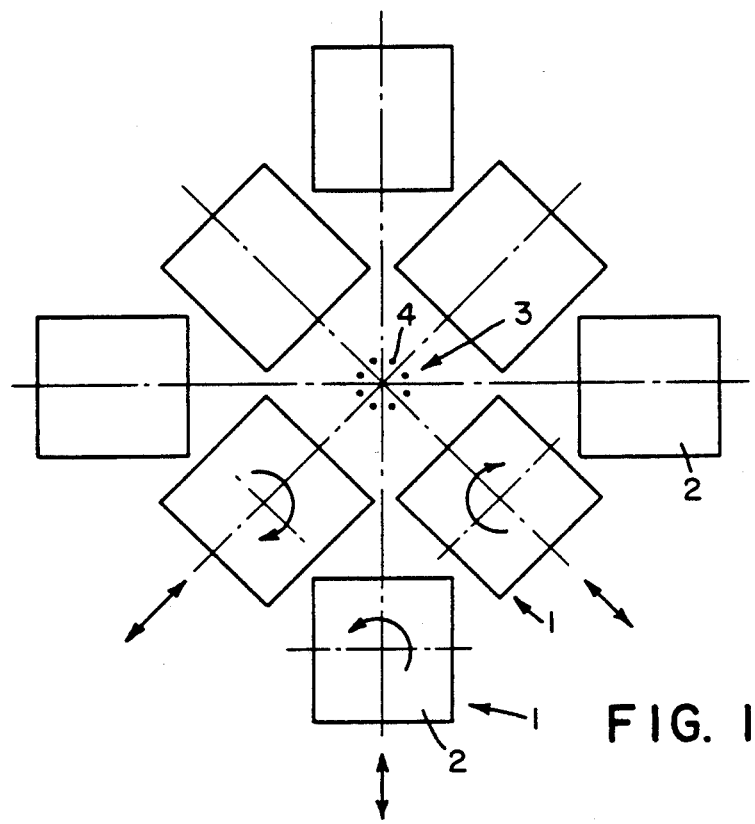
FIGS. 1 and 2 show a preferred apparatus having 8 columns and shifting in a radial direction, at different points in time.

FIG. 1 depicts a much simplified top view of vertically arranged columns 1 with objects to be irradiated 2 and a rod-shaped source of radiation 3, which is composed of several individual elements 4, by way of illustration rods with Cobalt-60. Half of the columns are moved relatively close to the radiation source and thereby shield at least partially the columns that are positioned further out. By turning 90 degrees step by step, all four sides of each column are turned to the source of radiation. A step-by-step 180 degree turn suffices when the requirements for dosage uniformity are less. In order to have sufficient room for the rotation, a part or all of the columns can be moved out a little to an intermediate position for a short time. Subsequently the positions are changed, i.e. the inner columns are moved out and the outer columns are moved in. The directions of the movement are indicated by arrows.

Figure 2:
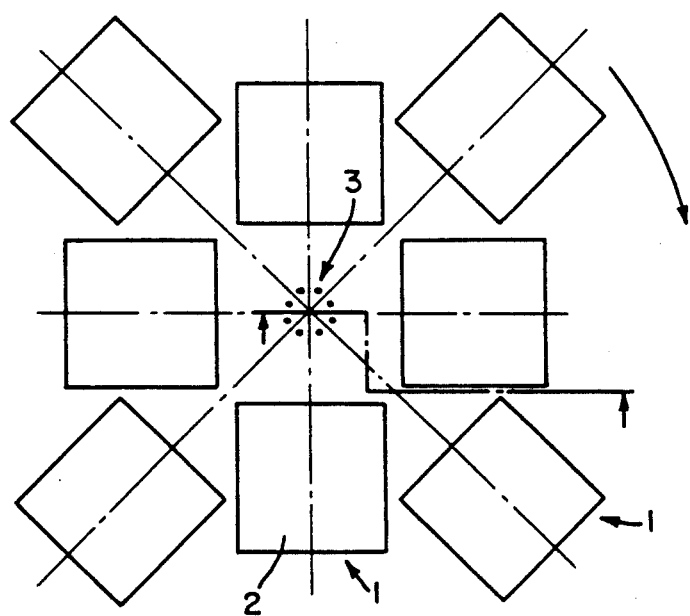

FIG. 2 depicts the preferred apparatus of the invention illustrated in FIG. 1 after the columns have moved. In this position the columns are also turned like described hereinafter. It is expedient that the direction of rotation is counter-clockwise. According to the foregone description, each column has turned two revolutions and has been moved to and fro once in a radial direction for a complete irradiation cycle. It is, however, also possible to move the columns to and fro after each 90 degree turn. Then each column has turned one revolution at the end of the irradiation cycle.

For easier loading and unloading of the objects, the entire technical system for halting and moving the objects can be arranged on a carousel which then brings them to the desired loading and unloading position. To compensate for uneven distribution of the individual elements 4 of the radiation source, the carousel can also be rotated continuously or pendulantly.

Figure 3:
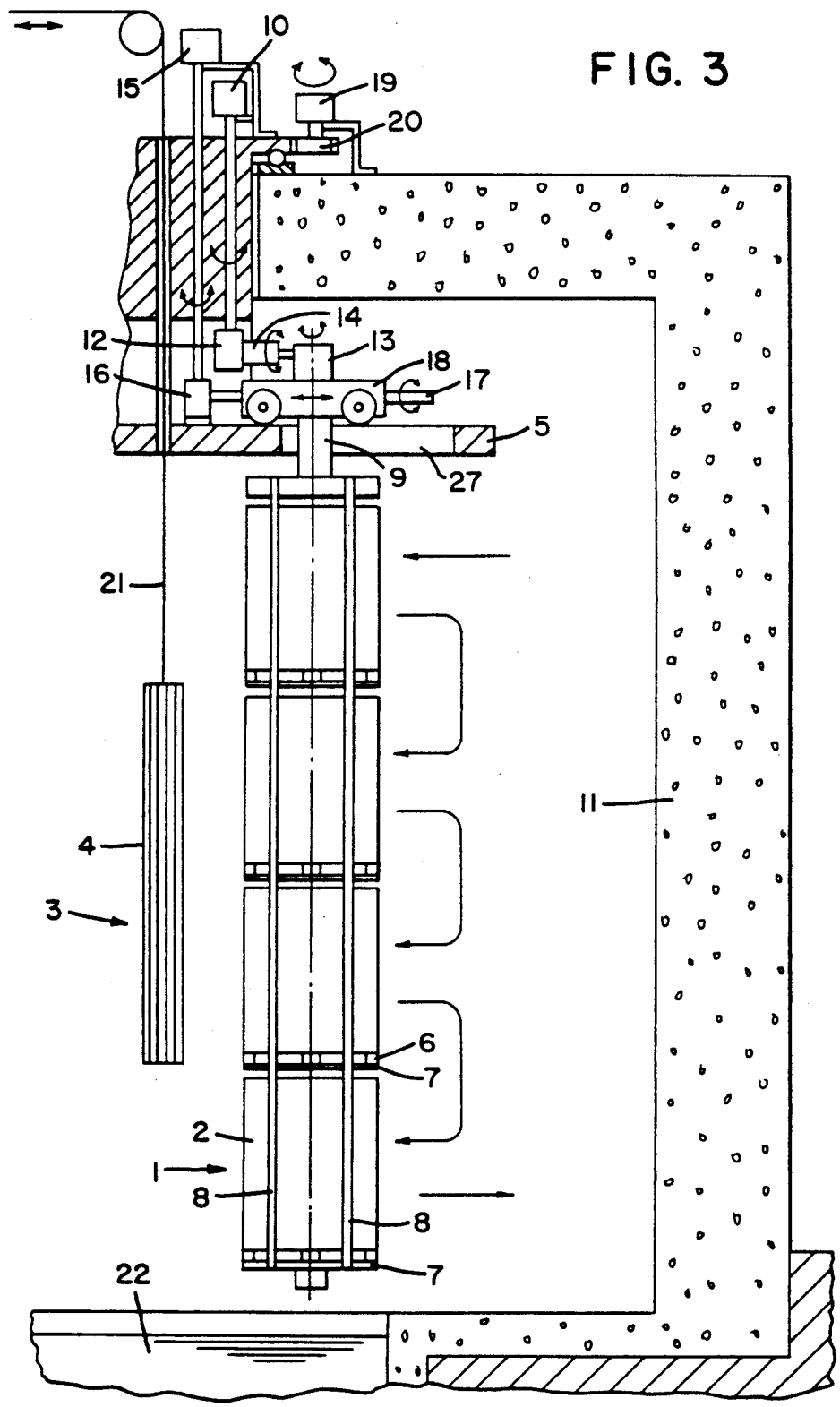
FIG. 3 shows the cross-section illustrated in FIG. 2 as a carousel arrangement.

FIG. 3 depicts a longitudinal-section of the invented apparatus shown in FIG. 2. Illustrated is a carousel with an overhead platform 5 and a column 1 with objects to be irradiated 2, which are resting on pallets 6 and are deposited on four carrying devices 7. Carrying devices 7 are held by outer supports 8, which are attached to a rotatable axle 9, supported in bearings. The possible linear movement of axle 9 is restricted by slit 27. A drive 10 for axle 9 lies outside shielding 11. The rotary movement of drive 10 is transmitted via two bevel drive gearboxes 12 and 13 to column 1. Transmission spindle 14 can be extended telescopically. Another drive 15 which moves a threaded spindle 17 via another bevel gearbox 16 is responsible for the linear movement of the columns. A nut, which is not illustrated herein, turns this rotational movement into a linear movement, which acts on car 18 running on rails. Another drive 19 moves the entire platform 5 via a beveled gear 20. In large plants an additional bearing support is usually required at the bottom of column 1. Radiation source 3, which is composed of a multiplicity of Cobalt-60 rods 4, hangs on a steel rope 21 and can be lowered in a water tank 22 via a source hoisting gear, which is not completely illustrated herein. The arrows on column 1 are to show how the objects to be irradiated 2 can traverse the column during the irradiation process. First the lower shipping unit is removed. Then the three remaining units are lowered one story. Finally an unirradiated shipping unit is placed in the top story. When radiation source 3 is in water tank 22 the reshifting can be carried out manually.

Figure 4:
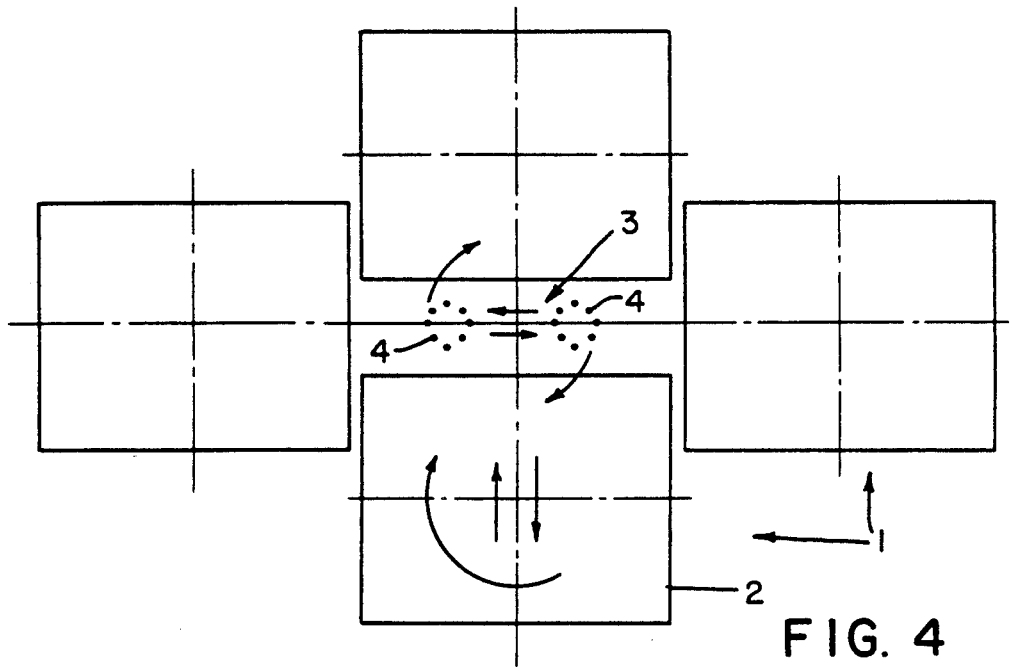
FIGS. 4 and 5 show a preferred apparatus having 4 columns, at different points in time.
Figure 5:
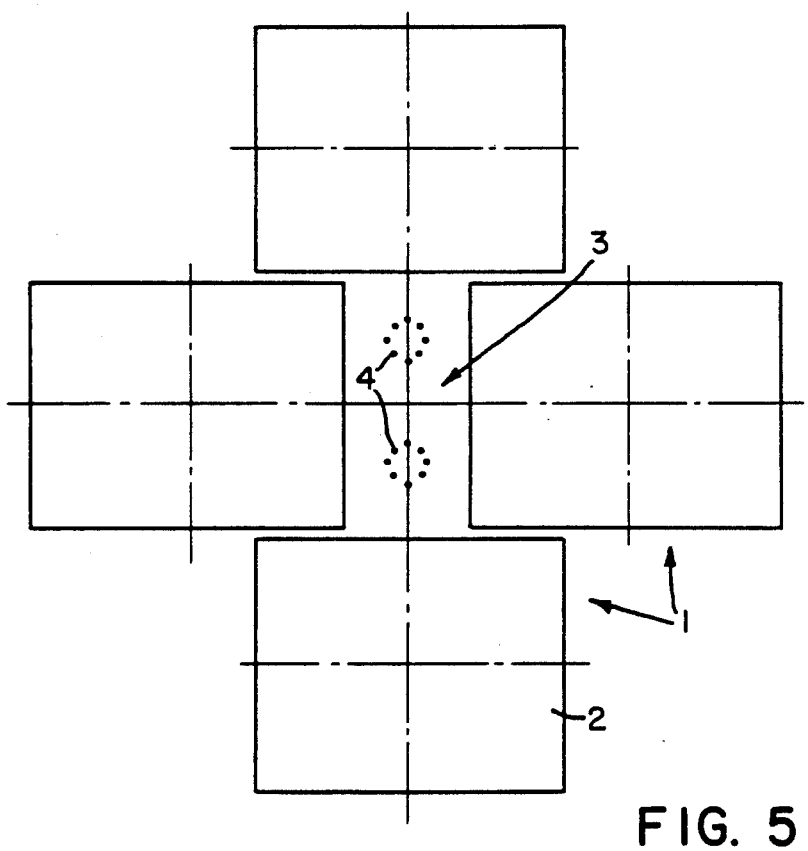

FIGS. 4 and 5 illustrate an arrangement having four columns 1. The individual elements 4 of the radiation source 3 are arranged in two groups which, as arrows indicate, can move toward each other. Moreover, radiation source 3 is rotatable as a unit. This measure can contribute to improved dosage uniformity. It also makes it possible to place a greater number of individual elements 4 in the relatively small inner space. The arrows on the cross-section of column 1 are intended to represent the to and fro movement of column 1 and the rotational movement. FIG. 5 only differs from FIG. 4 by a different state of movement: the inner columns have been moved to a position at a distance from the radiation source and the outer ones to a position near the radiation source. Moreover, the source of radiation has been turned 90 degrees. The next step would be turning, by way of illustration, 90 degrees. To do so, however, columns 1 have to be brought to an intermediate position so that they do not impede each other. Another possibility to irradiate the columns from all sides is to have columns 1 circle radiation source 3 in circumferential direction, by way of illustration by means of a mono or a multiple rail system.

Figure 6:
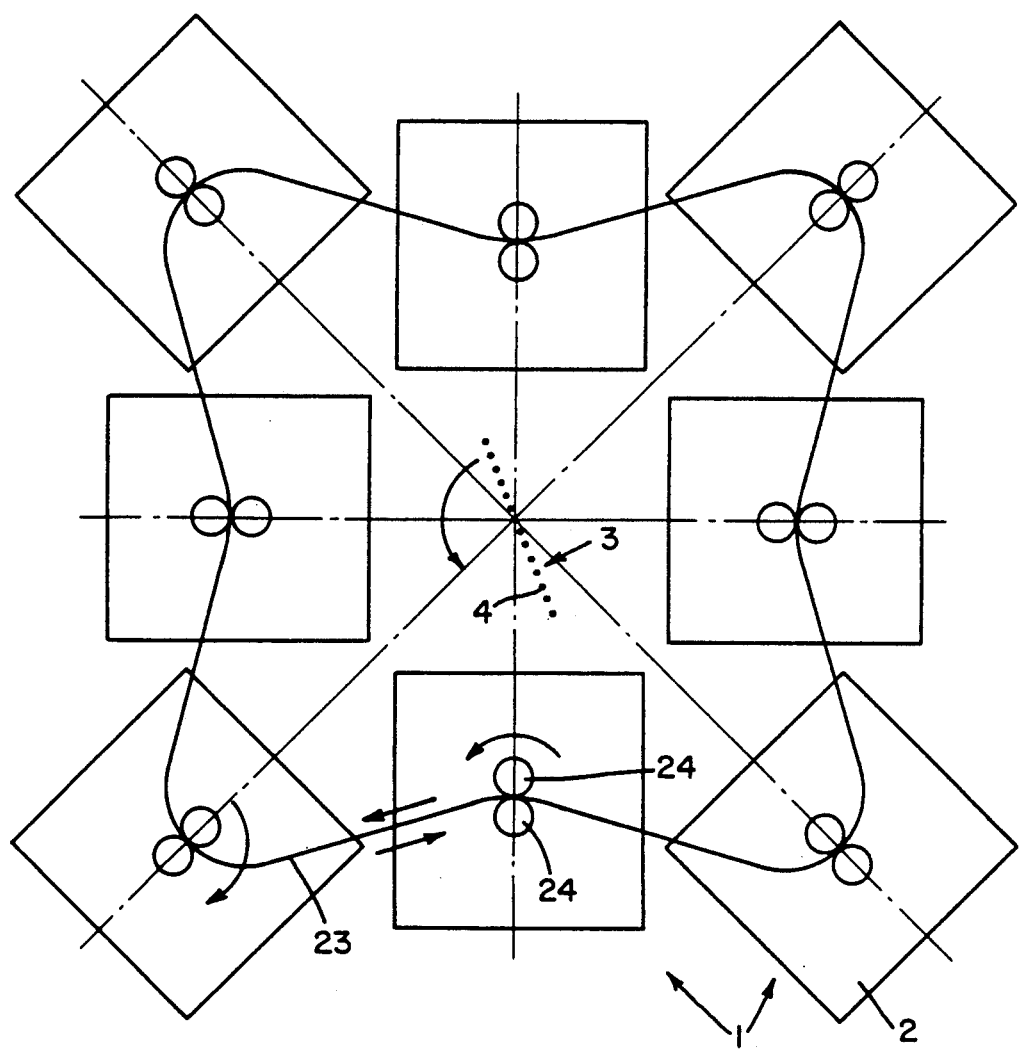
FIG. 6 shows a preferred apparatus with a monorail.

FIG. 6 shows the principle construction of a monorail system for an invented apparatus having eight columns. The course of the track is illustrated in a simplified manner by line 23. The columns are moved on this track by guide wheels 24. The columns are connected in a prior art manner by means of links and have drives for linear and rotational movement. A particular advantage of this monorail system is that each column can be brought, by means of an appropriate regulation, to a stationary conveying device for loading and unloading. Movement is possible in any direction and can change during irradiation. What is important is that a position near the radiation source and one at a distance from the radiation source is taken up at least once during an irradiation cycle. Other conveying devices, besides a monorail, can, of course, be employed in order to reach these positions. With the shape of radiation source 3 it is to be made clear that practically any shape of the radiation source is suitable for the preferred and apparatus as long as it fits into the inner space of the apparatus. The arrangement of the individual elements 4 of the radiation source is that as a plane source. In order to avoid non-uniformity, the radiation source can be rotated around its center axis. Rotating in steps with intermediate stops lying between the lines which form the axis of rotation of the radiation source and the columns is particularly advantageous, because the reciprocal radiation absorption of the individual elements 4 can hardly effect the efficiency of the invented apparatus.

Figure 7:
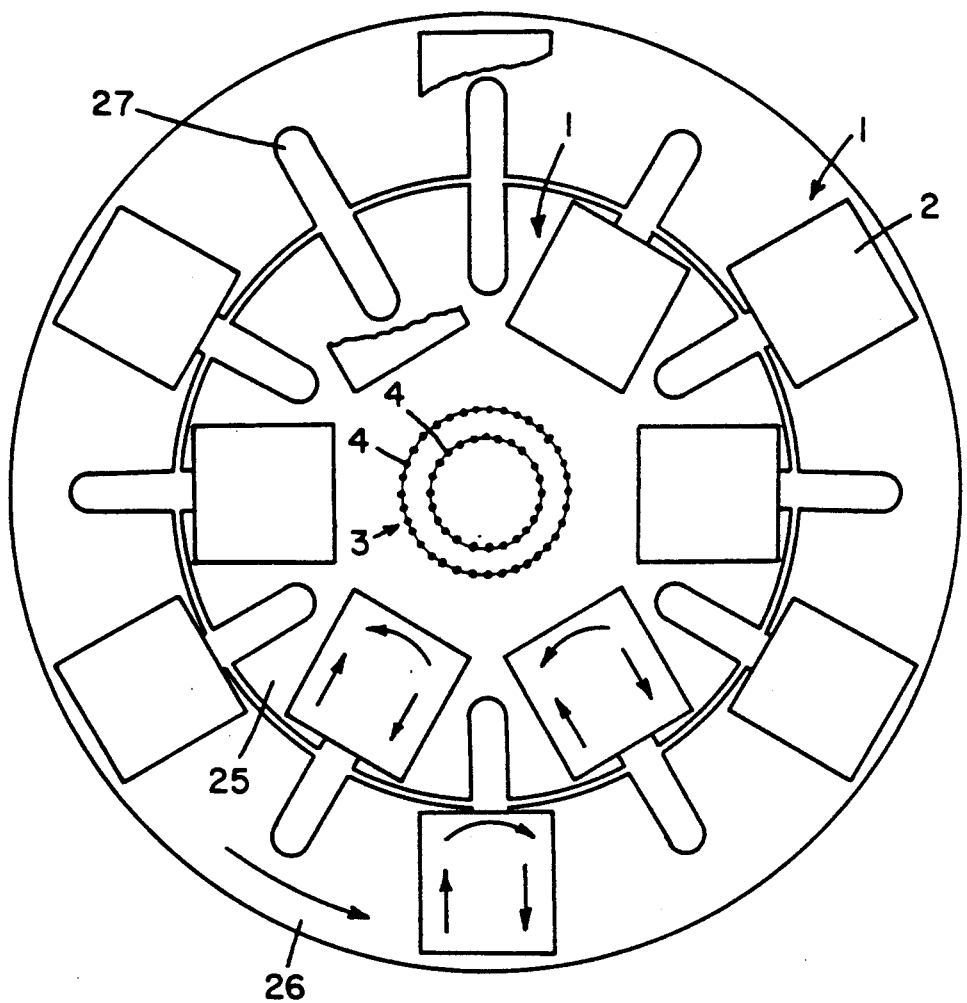
FIG. 7 shows an arrangement with 12 columns and a rotatable platform for six columns.

FIG. 7 depicts a special type of carousel. There is a certain similarity between this figure and FIG. 3. The carousel platform here is divided into a stationary inner ring 25 and a rotatable outer ring 26. Columns 1 are shifted to and fro in a radial direction between these two rings. Slits 27 indicate the maximum inner and outer positions to be reached. The outer position is selected in such a manner that columns 1 do not impede each other when platform 5 makes a short rotational movement. During irradiation these columns can be moved very close to the columns which are near the radiation source. Radiation source 3 is illustrated here as a double-row cage arrangement.

Figure 8:
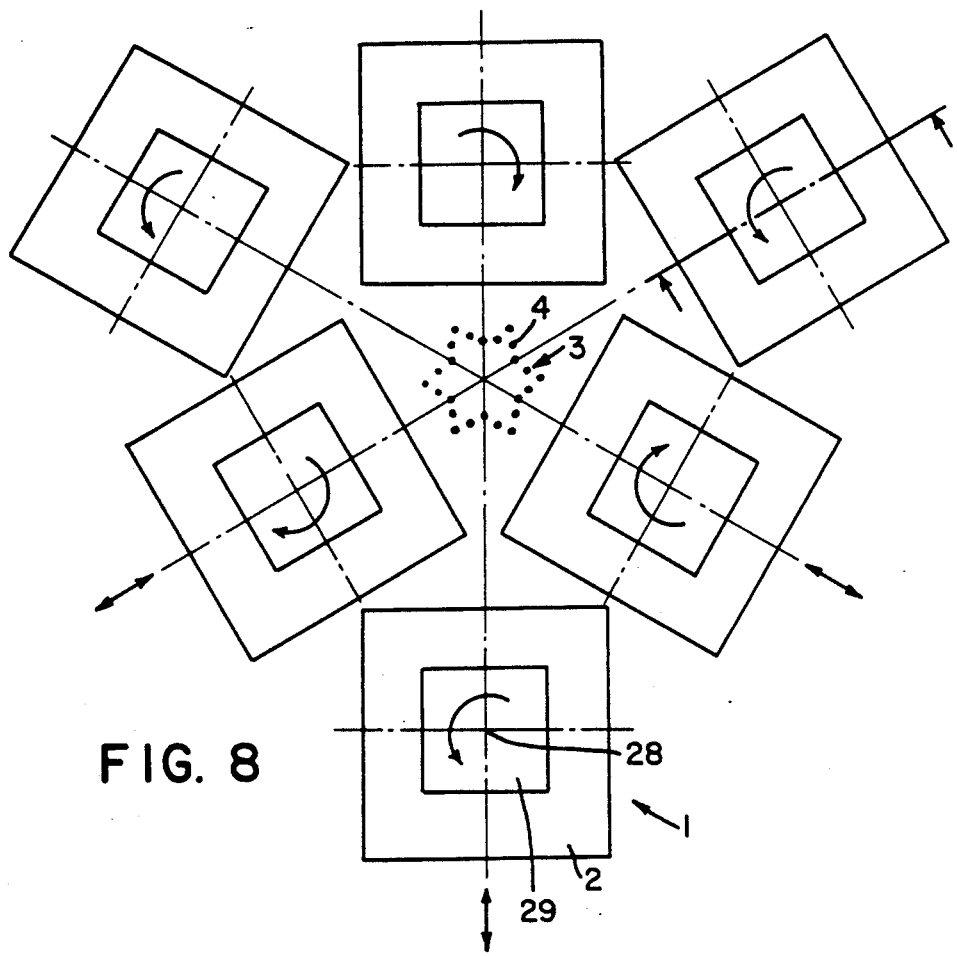
FIG. 8 shows an arrangement with an empty space in the center of the objects to be irradiated.

FIG. 8 depicts an arrangement having six columns 1 arranged around a radiation source 3 having a star-shaped cross-section. Said columns have an empty space 29 in the area of their axis of rotation 28.

Figure 9:
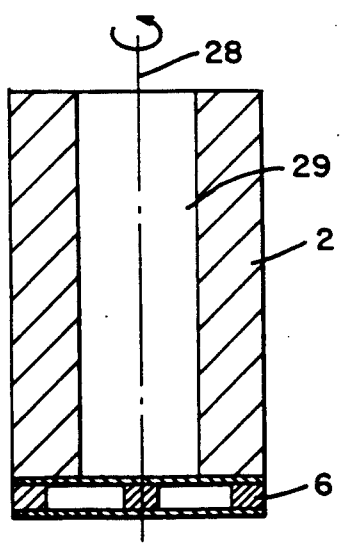
FIG. 9 shows a shipping unit from FIG. 8.

FIG. 9 depicts said empty space in a longitudinal crosssection of a shipping unit. The objects to be irradiated 2 are arranged in the shape of a wall and stand on a pallet 6. Columns 1 preferably contain several such shipping units. All shipping units of a column have preferably been provided with an empty space. The objects to be irradiated of the adjacent columns 1 may be arranged without an empty space and the density may be great or little.

Instead of the empty space 29 illustrated in FIGS. 8 and 9, objects to be irradiated having less density can be arranged in the area around the axis of rotation 28 and objects to be irradiated having great density can be arranged in the peripheral area. The density gradient running radially to axis of rotation 28 may be continually variable or in steps with increasing distance from the axis of rotation. This has a favorable effect on efficiency and dosage uniformity.

FIG. 10 depicts a sectional view of an arrangement having eight columns 1 which illustrates different variants of additional shielding devices 30, 31, 32. Shielding devices 30, 31, 3 run parallel to the axis of rotation of the column and are approximately as long as the columns. Dosage uniformity, which is already very good even without these devices, can be further improved with said shielding devices. It is expedient to arrange said shielding devices 30, 31, 32 in such a manner that they only weaken the path of radiation further where experience has shown an overdosage would occur. The shape of said devices must be adapted to the size and density of the shipping unit, the shape of the radiation source and their site. Shielding devices 30 are arranged very close to the objects to be irradiated 2 in the near position of the columns. In order to carry out a rotational movement of columns 1, these have to be moved radially outward for a short time or shielding devices 30 have to be moved inward. In comparison, shielding devices 31 are arranged so far to the interior that an unimpeded rotational movement of the columns is possible in their end positions. Shielding devices 32 are composed of a multiplicity of thin-walled pipes 34. This form and modus operandi is illustrated in detail in FIGS. 11 and 12. Some of said pipes 34 can, by way of illustration, be filled with water or mercury and thus adjust the shielding effect very quickly to the product to be irradiated. To a limited extent, a variability of form and of site can be simulated in this manner. Pipe 34 can be supplied from container 35 containing fluid 36 into which pipe 34 dips. With the aid of air from conduit 37, pipe 34 can be filled in a simple manner and emptied again by slackening.

Shielding devices 30, 31, 32 may also be arranged before the columns standing in the position at a distance from the radiation source. In that case, they, however, would have to be moveable. Such mobility is not necessary when the arrangement of FIG. 6 is selected.

Figure 13:
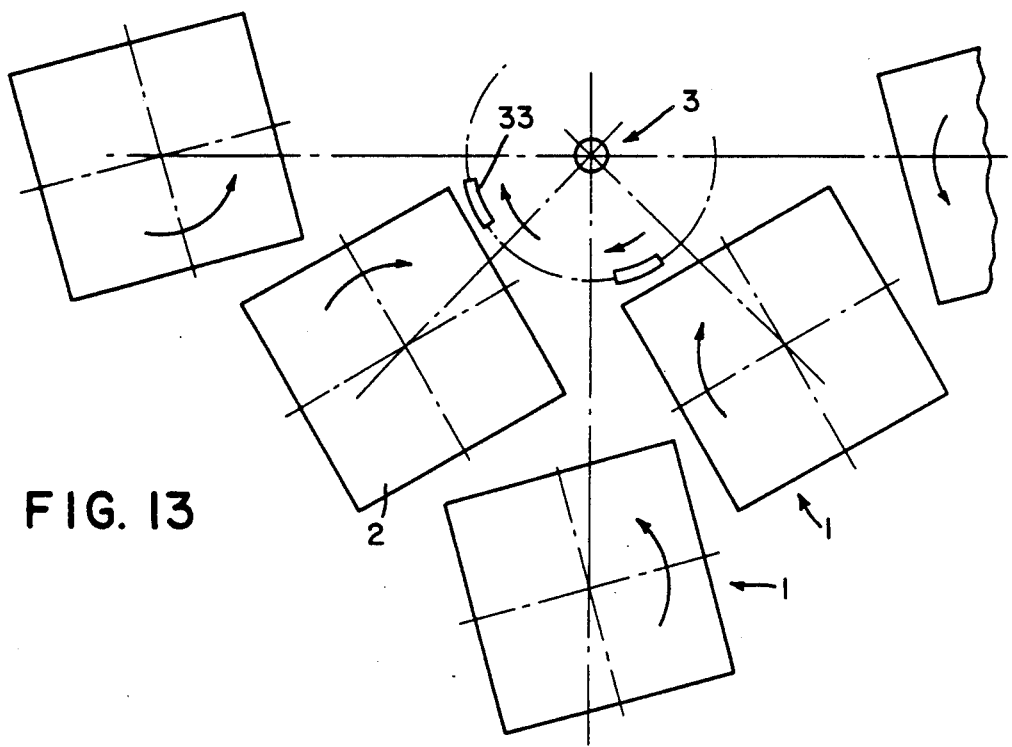
FIGS. 13 and 14 show a section of the preferred apparatus having 8 columns and moveable shielding devices, at different points in time.
Figure 14:
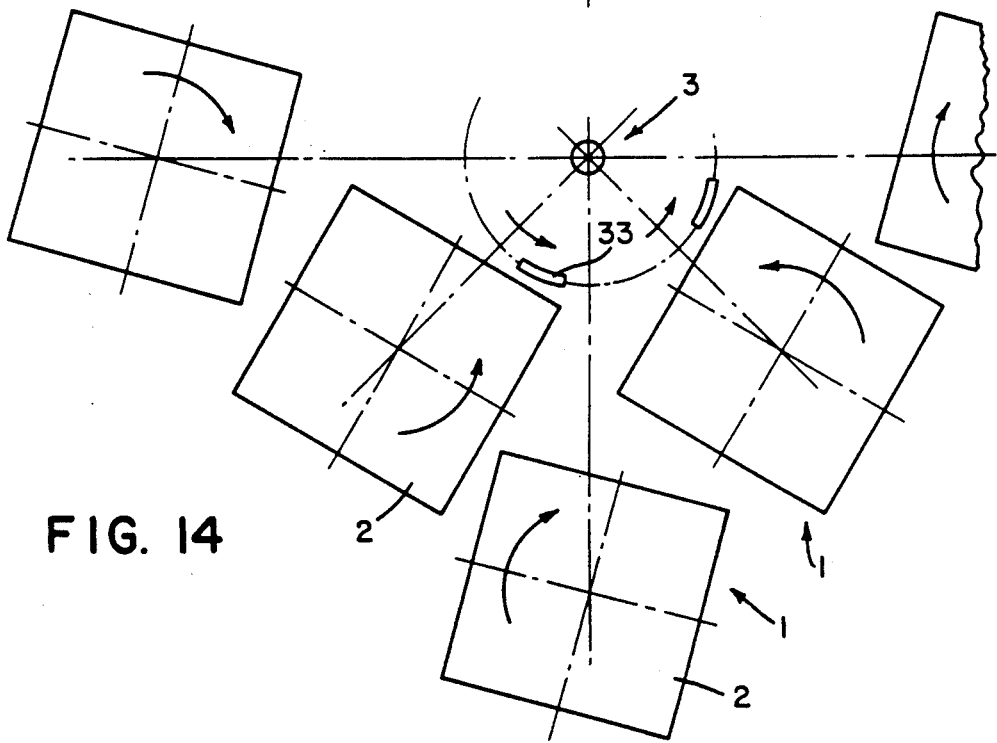

FIGS. 13 and 14 depict a sectional view of an arrangement of eight columns 1 in a different state of movement in a pendulant rotational movement of columns 1.

FIG. 13 shows the state following a right turn of the inner column in a small angle. In this state, near the most inward protruding corner is a shielding device 33, whose effect is not restricted solely to the corner, but also effects the peripheral area of the lateral parts lying behind it. This weakening also effects the outer columns. In order to irradiate all the lateral parts in the same manner, the inner columns are then turned a little to the left. Shielding devices 33 are also simultaneously rotated on a circular path around the axis of the radiation source in such a manner that they are now once again arranged before the farthest inward lying corner of column 1.

FIG. 14 illustrates this state. This procedure is repeated for each 90 degree or 180 degree turn. In this manner an excellent dosage uniformity is achieved even for very heavy products. Shielding devices are also advantageous when the objects to be irradiated are packed in a special manner as described in FIGS. 8 and 9.

The present invention is especially suitable for large industrial irradiation plants. The size of the shipping units lies preferably between 0.1 to 20 cubic meters. Large units are particularly suitable for irradiation products of little density. Thus by way of illustration an efficiency of more than 50% was determined for an eight-meter cubic-shaped unit having a density of 0.15 g/cm$^3$, whereby a ratio of maximum to minimum dosage of approximately 1.15 to 1.3 can be achieved. With their density and suitable type and size of the shipping units efficiency can even lie above 60%. A particular advantage of the present invention is that products having the same or different density can be irradiated simultaneously with the same dosage or varying dosages.

The foregoing description illustratively describes the invention and with its teachings, many such modifications and adaptations can be made or performed by the skilled artisan. Accordingly, it is the inventor's intent to include such modifications and adaptations within the scope of the appended claims.

What is claimed is:

1. A process for irradiating a plurality of objects arranged in a plurality of shipping units, each shipping unit being defined by an axis, said process comprising the steps of:

emitting ionizing radiation from a radiation source,
   arranging the shipping units so that respective axes extend parallel to a direction of conveyance of the shipping units about the radiation source,
   positioning a first shipping unit near the source and a second shipping unit at a distance from the source so that portions of the first shipping unit provide a shielding effect upon respective portions of the second shipping unit, said shielding effect near the axis of the second shipping unit being less than the shielding effect in the peripheral area of the second shipping unit, and
   rotating the shipping units around said axes so that the objects packaged therein are irradiated from at least two sides, and
   interchanging the positions of said first and second shipping units by movement relative to the radiation source, thereby causing the second shipping unit to provide a shielding effect upon respective portions of the first shipping unit, said shielding effect near the axis of the first shipping unit being less than the shielding effect in the peripheral area of the first shipping unit, whereby said shielding effect causes substantially equal irradiation of the objects during the irradiation process.

2. A process as defined in claim 1, wherein said rotating the shipping units comprises irradiating the objects from at least four sides.

3. A process as defined in claim 1, wherein said interchanging of positions of the shipping units comprises moving the shipping units radially relative to the source of radiation.

4. A process as defined in claim 1, wherein said interchanging of positions of the shipping units comprises moving the shipping units in a circumferential direction.

5. A process as defined in claim 1, wherein said arranging of shipping units comprises arranging the shipping units in at least two columns.

6. A process as defined in claim 5, wherein the objects are arranged in such a manner that an empty space is created near an axis of the columns.

7. A process as defined in claim 5, wherein a density of objects near the axis of said columns is less than near a periphery of the column.

8. A process as defined in claim 1, wherein said interchanging of positions of the shipping units comprises moving the second shipping unit in a circumferential direction.

9. A process as defined in claim 1, further comprising continuously rotating the shipping units around said radiation source.

10. A process as defined in claim 1, further comprising rotating the shipping units step by step around said radiation source.

11. A process as defined in claim 1, further comprising rotating the shipping units pendulantly around said radiation source.

12. A process as defined in claim 1, wherein said interchanging of the positions of the shipping units is continuous during irradiation.

13. A process as defined in claim 1, wherein said interchanging of positions of said shipping units comprises regulation by a process computer, which calculates the dosage absorbed at the individual positions in order to regulate said movement.

14. A process as defined in claim 1, wherein said interchanging of the positions of the shipping units is step by step during irradiation.

15. An apparatus for irradiating a plurality of objects arranged in a plurality of shipping units, each shipping unit being defined by an axis, said apparatus comprising:
carrying means for carrying at least four shipping units containing the objects around a source of radiation, at least two shipping units being arranged in a position near the radiation source and at least two shipping units being arranged in a position at a distance from the radiation source in such a manner that the shipping units in the near position shield the shipping units in the distant position whereby the shielding effect is less in the center of the shipping units in the distant position than in a periphery.

16. An apparatus as defined in claim 15, wherein the carrying means further comprises at least four carrying devices each being rotatable around an axis.

17. An apparatus as defined in claim 16, wherein the carrying devices are movable in a radial direction relative to the source of radiation.

18. An apparatus as defined in claim 16, wherein the carrying devices are rotatable around the source of radiation.

19. An apparatus as defined in claim 16, wherein the carrying devices are movable radially and are rotatable around the source of radiation.

20. An apparatus as defined in claim 16, further comprising a radiation source having a symmetrical cross-section with "n" edges, wherein "n" equals the number of carrying devices arranged side by side, an integral part thereof or an integral multiple thereof.

21. An apparatus as defined in claim 16, wherein several carrying devices are arranged in the direction of the axis of the column.

22. An apparats as defined in claim 15, further comprising a carousel on which at least part of the carrying means is arranged.

23. An apparatus as defined in claim 15, further comprising a rotatable source of radiation.

24. An apparatus as defined in claim 15, further comprising a source of radiation having individual elements arranged in subgroups which subgroups can be moved relative to each other.

25. An apparatus as defined in claim 15, further comprising a plurality of shielding devices arranged between the radiation source and said carrying means whereby radiation emitted lateral of a flow line running from the center of the radiation source to the centerof the objects to be irradiated is further shielded.

26. An apparatus as defined in claim 25, wherein the shielding devices are moveable.

27. An apparatus as defined in claim 25, wherein the shielding devices are mutable.

* * * * *